(12) United States Patent
Larsson et al.

(10) Patent No.: US 8,372,339 B2
(45) Date of Patent: Feb. 12, 2013

(54) STERILIZATION DEVICE, STERILIZATION PROCESS, VAPORIZING SYSTEM AND USE OF SUCH VAPORIZING SYSTEM

(75) Inventors: Joakim Larsson, Halmstad (SE);
Bjarne Pedersen, Eldsberga (SE);
Mats-Åke Åhlund, Gullbrandstorp (SE);
Stefan Nilsson, Getinge (SE)

(73) Assignee: Getinge Sterilization AB, Getinge (SE)

( * ) Notice: Subject to any disclaimer, the term of this patent is extended or adjusted under 35 U.S.C. 154(b) by 685 days.

(21) Appl. No.: 12/449,850

(22) PCT Filed: Mar. 1, 2007

(86) PCT No.: PCT/SE2007/000202
§ 371 (c)(1),
(2), (4) Date: Aug. 31, 2009

(87) PCT Pub. No.: WO2008/105696
PCT Pub. Date: Sep. 4, 2008

(65) Prior Publication Data
US 2010/0086438 A1    Apr. 8, 2010

(51) Int. Cl.
*A61L 9/00* (2006.01)
*A62B 7/08* (2006.01)
*B03C 3/16* (2006.01)
*B01D 46/00* (2006.01)
*B01D 50/00* (2006.01)
*F24F 13/078* (2006.01)

(52) U.S. Cl. .......... 422/26; 422/1; 422/28; 422/30; 422/33; 422/124; 422/305; 95/283; 95/72; 55/315; 55/338; 55/467.1; 55/476; 55/482.1; 454/234; 454/235; 96/227

(58) Field of Classification Search ........... 422/1, 28, 422/30, 33, 124, 305; 95/283, 72; 55/315, 55/338, 467.1, 476, 482.1; 454/234, 235; 96/227

See application file for complete search history.

(56) References Cited

U.S. PATENT DOCUMENTS

| 4,727,871 A | 3/1988 | Smargiassi et al. |
| 5,480,610 A | 1/1996 | Birkholz et al. |

(Continued)

FOREIGN PATENT DOCUMENTS

| EP | 0 908 189 | 4/1999 |
| EP | 1 300 630 | 4/2003 |
| EP | 1 647 284 | 4/2005 |
| FR | 2 745 198 | 8/1997 |
| WO | WO 98/33532 | 8/1998 |

(Continued)

OTHER PUBLICATIONS

Search Report dated Jun. 18, 2010 issued in corresponding European Application No. 07716027.3.

*Primary Examiner* — Jill Warden
*Assistant Examiner* — Monzer Chorbaji
(74) *Attorney, Agent, or Firm* — Harness, Dickey & Pierce, P.L.C.

(57) ABSTRACT

The invention discloses a sterilization device (1), to sterilize media, equipment and/or decontamination of waste material, said sterilization device (1) comprising a chamber (2), at least one exhaust line (6) arranged to said chamber (2) and at least one gas generator arranged to said chamber (2), at least two sterile filters (8a, 8b) arranged in series in the exhaust line (6), at least one vacuum means (7) connected to the chamber (2) via said exhaust line (6) and said at least two filters (8a, 8b). At least one heating means (9) is arranged to said exhaust line (6) between said two sterile filters (8a, 8b) in order to vaporize condensate that develops between the filters. Furthermore, it is disclosed a sterilization process for sterilization of media, equipment and/or decontamination of waste material, a vaporizing system (12) of a sterilization device and use of such a vaporizing system (12) in a sterilization device.

9 Claims, 2 Drawing Sheets

U.S. PATENT DOCUMENTS

| | | | |
|---|---|---|---|
| 5,523,052 A * | 6/1996 | Bridges et al. | 422/22 |
| 5,840,248 A * | 11/1998 | Ongaro | 422/26 |
| 7,510,470 B2 * | 3/2009 | Arts | 454/187 |
| 2003/0145806 A1 | 8/2003 | Tokutake et al. | |
| 2005/0013726 A1 | 1/2005 | Hill et al. | |

FOREIGN PATENT DOCUMENTS

| | | |
|---|---|---|
| WO | WO 99/49903 | 10/1999 |
| WO | WO 2005/014054 | 2/2005 |
| WO | WO 2005/014054 A2 * | 2/2005 |

* cited by examiner

STERILIZATION DEVICE, STERILIZATION PROCESS, VAPORIZING SYSTEM AND USE OF SUCH VAPORIZING SYSTEM

FIELD OF THE INVENTION

The present invention relates to a sterilization device to sterilize media, equipment and/or decontamination of waste material. Furthermore, the present invention discloses a sterilization process for sterilization of media, equipment and/or decontamination of waste material with at least one vacuum-steam phase within a chamber of a Sterilization device. The invention also discloses a vaporizing system of a sterilization device and the use of such a system.

TECHNICAL BACKGROUND

Laboratories, such as for example laboratories with bio safety level 3 and 4 (BSL 3 and BSL 4), research facilities, bio-containment suites and hospitals need autoclaves for sterilization of media, equipment and/or decontamination of waste material. Both "wet" wastes such as blood, organs, animal parts etc. and "dry" wastes such as animal cages, tools etc. are being treated in autoclaves. Essentially the autoclave shall kill dangerous microorganisms such as germs and viruses.

The pathogenic nature of the waste material from such facilities coupled with the use of the autoclave as a barrier between the facility and the outside world places special requirements on the autoclave design and processes used.

Sterilization is carried out in a manner known per se in pressure tight autoclaves, which can be charged with steam in a vacuum-steam process. In this process, the container, which are filled with the risky waste and equipments, is filled a plurality of times with steam and is then evacuated close to a vacuum level between each occasions as far as possible. After sterilization has taken place the chamber is once again evacuated, to accelerate the drying of the articles loaded inside the chamber. As pressure equalizer air is provided. The sterilized articles may now be removed.

It is very important that everything that leaves the autoclave is sterilized; not only the articles that are placed within the autoclave but also everything that leaves the autoclave via the different exhaust lines. At the top of the chamber usually an exhaust line is arranged where not condensate can be exhausted. However at the same time steam and airborne organisms may escape during the evacuation of the chamber, before they are sterile, especially under the pre-vacuum/steam process, since the vacuum device is connected to the exhaust line.

An incinerator may be arranged between the chamber and the vacuum means to enable sterilization of the steam/gas. Using incinerators is an effective and an easy way to kill organisms, since the process comprises very high temperature (several hundreds of ° C.). However, such a device may be more energy consuming and less cost effective. It is also bulky and not generally accepted.

Alternatively, a sterile filter may be used.

U.S. Pat. No. 5,480,610 discloses an apparatus and process for disinfection of waste in autoclaves and to odours neutralization of the exhaust vapours. It comprises two filters connected in series. The first filter is a prefilter and the second one is a sterile filter. The condensate produced by the filters, after disinfection is separately discharged into the waste water line.

However, for dangerous organism, disinfection is not enough and also the handling has to be done in a safe manner.

Hence, there is still a need to improve the handling and safety of the medium evacuated from the chamber.

SUMMARY OF THE INVENTION

In view of the above, an objective of the invention is to solve or at least reduce the problems discussed above. Hence, the invention according to claim discloses a sterilization device, to sterilize media, equipment and/or decontamination of waste material, said sterilization device comprising a chamber, at least one exhaust line arranged to said chamber and at least one gas generator arranged to said chamber, at least two filters arranged in series in the exhaust line, at least one vacuum means connected to the chamber via said exhaust line and said at least two filters. Wherein between said two filters at least one heating means is arranged to said exhaust line to vaporize condensate that develops between said two filters and that said filters are sterile filters. Through sterile filters, gas such as for example steam or air may pass through. By the term of sterile filters, they may be regarded as hydrophobic filters. Therefore a heating means is used to vaporise the condensate so that the steam can pass through the filters and the rest of the system without stopping the process for example for evacuating the condensate into a separate tank (which is cost intensive since the condensate has to be killed after process) or pump it back to the chamber (which may cause pressure problem within the system). The sterile filter may be a sterilizing grade filter according to the ASTM F838-83 guideline. Several filters may be arranged after each other in series and between every two filters one or more heating means may be arranged.

Said exhaust line may be arranged at an upper region of said chamber so that the air/gas easily may be evacuated.

Preferably, said exhaust line may be arranged at least above a water level in said chamber, so that no water/condensate, which may be gathered at the bottom of the chamber are evacuated through the exhaust line with the arranged filters.

Said heating means may be adapted to be shut-off. The heating means may be activated intermittent. This when the sterilization process may be proceeded for a longer time, wherein the heating means can be shut-off in order to save energy. The heating means may also be used separately before the sterilization process within the chamber starts, in order to preheat the exhaust line. This to enable less condensate to be developed during the process. Since it is known that most condensate may be developed during the pre-evacuations.

Said heating means may be a heat exchanger. It may for example use gas such as saturated steam as a heat source.

Said heating means may alternatively be an electrical heating device. For example a heat shield, a winding or a similar device, which may be arranged peripherally at the exhaust line.

Said heating means may be arranged at the level, where the condensate is gathered between said filters. Here the heating means will have the most effect to the condensate. However, the heating means may be arranged at least partly of the length extension between the filters, so the whole exhaust line is kept warm and the condensate development may be reduced.

Said at least two sterile filters are essentially of the same type. The advantage is that the service will be improved and the number of different components being reduced and by integrity test the same test equipment may be used.

However, said at least two sterile filters may have decreasing permeability for example decreasing pore size. Hereby the security level may be improved.

At least one of said sterile filters may be automatically individually tested for defects with an integrity tester. For instance a sterile filter may be fluidly connected to such a tester using pressure as defect tester. The integrity tester may be a special instrument, which is arranged to the system during the test or it may be integrated within the system.

According to a second aspect of the invention a sterilization process is provided for sterilization of media, equipment and/or decontamination of waste material with at least one vacuum-steam phase within a chamber with an exhaust line, of a sterilization device, comprising the steps of;

loading the chamber with media, equipment and/or decontamination of waste material which are to be sterilized,
pre-evacuating the chamber of air with a vacuum means at least once,
introducing steam into the chamber after each pre-evacuation, via a input line connected to a gas generator,
heating the chamber and its content with steam until sterilizing temperature and pressure is attained,
maintaining the steam pressure and temperature until the content of the chamber is sterilized,
evacuating the chamber until the content of the chamber is essentially dry,
equalizing chamber pressure, during at least said pre-evacuation of said chamber by suction the steam/air from the chamber, said steam/air is filtered through at least two sterile filters arranged in series, wherein condensate developed between said two sterilisation filter are heated by a heating means arranged at the exhaust line, to vaporise said condensate between said filters. Such a process may exhibit similar advantages and components as the sterilization device above.

Said vaporized condensate may pass the second filter downstream.

Said vaporized condensate and condensate developed after the second filter may pass out in the outlet. Said at least two sterile filters may be essentially of the same type, or said at least two sterile filters may have decreasing permeability for example decreasing pore size.

Said heating means may be adopted to be shut-off and the heating means may be a heat exchanger or an electrical heating device with the same purpose as the heating means mentioned above about the sterilization device.

According to an another aspect of the invention a vaporizing system is provided of a sterilization device comprising a chamber wherein media, equipment and/or decontamination of waste material are loaded which shall be sterilized, at least one exhaust line arranged to said chamber, further comprising a gas generator connectable to said chamber, and a vacuum means connectable to said chamber. At least two sterile filters are arranged to said exhaust line, wherein said vaporizing system comprises at least one heating means, being arranged between said two sterile filters and arranged to said exhaust line to at least heat the condensate, which develops inside the exhaust line between said two sterile filters, to vaporization.

Such a vaporizing system may exhibit similar advantages and components as the sterilization device above.

According to another aspect of the invention it is accomplished to use a vaporizing system in a sterilization device. An advantage is that the vaporizing system may be used in an existing sterilization device where no vaporizing system is built in.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated.

Other objectives, features and advantages of the present invention will appear from the following detailed disclosure, from the attached dependent claims as well as from the drawings.

BRIEF DESCRIPTION OF THE DRAWINGS

Currently preferred embodiment of the present invention will now be described in more detail, with reference to the accompanying drawings, wherein.

DETAILED DESCRIPTION OF PREFERRED EMBODIMENTS

Figure 1:
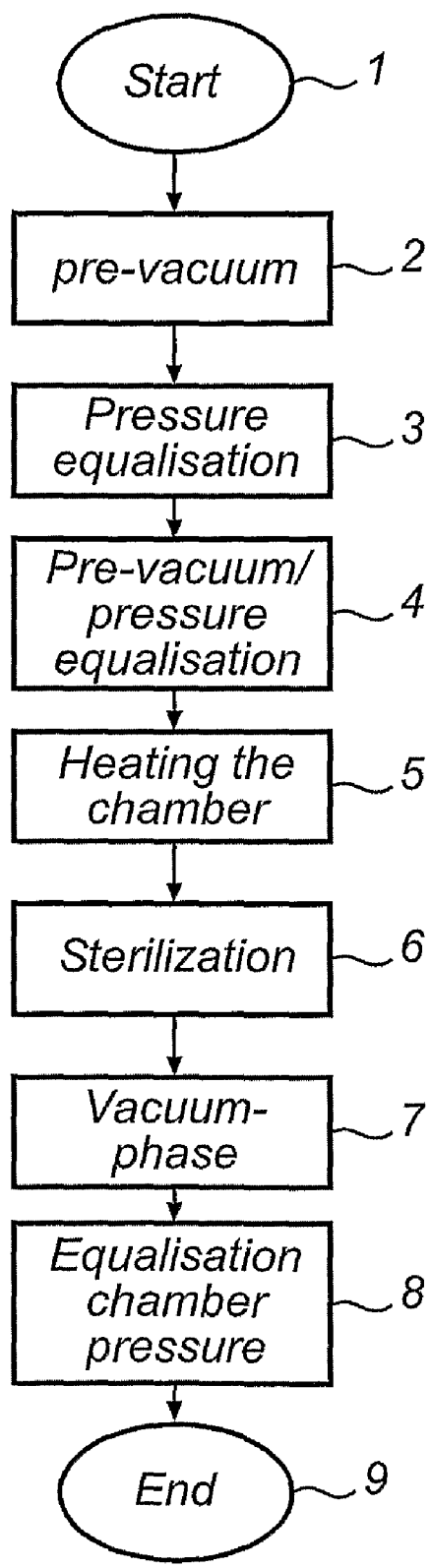
FIG. 1 discloses a process map over the sterilization process.

The above, as well as additional objects, features and advantages of the present invention, will be better understood through the following illustrative and non limiting detailed description of preferred embodiments of the present invention, with reference to the appended drawings, where the same reference numerals will be used for similar elements, wherein:

FIG. 1 shows the sterilization process, which is taken place within a sterilization device for example an autoclave. Hereinafter the sterilization device is referred to as an autoclave. However, it shall be noticed that it could be any kind of sterilization device. In step 1 the process starts. The chamber of the autoclave has been loaded with different kind of articles/objects, which are supposed to be sterilized and decontaminated. It may be media, equipment and/or dry and wet waste, which contain dangerous viruses and/or organism such as bacteria. Step 2 comprises the first pre-vacuum phase, which is achieved by using a vacuum means for example a vacuum pump. Essentially most of the air is removed from the chamber. During this step dangerous organism may also escape through the exhaust line before they are sterilized. How this problem is solved will be discussed together with FIGS. 2 and 3. As pressure equalizer in step 3, steam is filled into the chamber. Step 2 and 3 may be implemented several times, as iteration—comprised in Step 4. For example after the chamber has been loaded the chamber may be evacuated up to ca 90% (step 2). To the remaining 10% air, gas is added (step 3) until the chamber is saturated. The chamber is then evacuated again for example up to 90% (step 2). To the remaining 10% gas is again added to the chamber (step 3). Normally this (step 2 and 3) is performed at least three times. Step 5 comprises heating the chamber with gas for example saturated steam until sterilization temperature and pressure has occurred. In step 6 sterilization of the load occur by keeping the temperature and the pressure for a certain time until the load (3) is sterilized. Common holding temperatures may be 121° C., at a pressure of 2 bar (absolute pressure) for 20 min or 134° C., at a pressure of 3 bar (absolute pressure) for 7 min for enabling sterilization to take place. However, it shall be noted that other temperatures, pressures and holding times may be used. At Step 7 vacuum is again applied to the chamber and its load 3 to decrease the drying time. At step 8 air may be used as a pressure equalizer for the chamber. In step 9 the sterilization process has ended and the load may be unloaded from the chamber.

Figure 2:
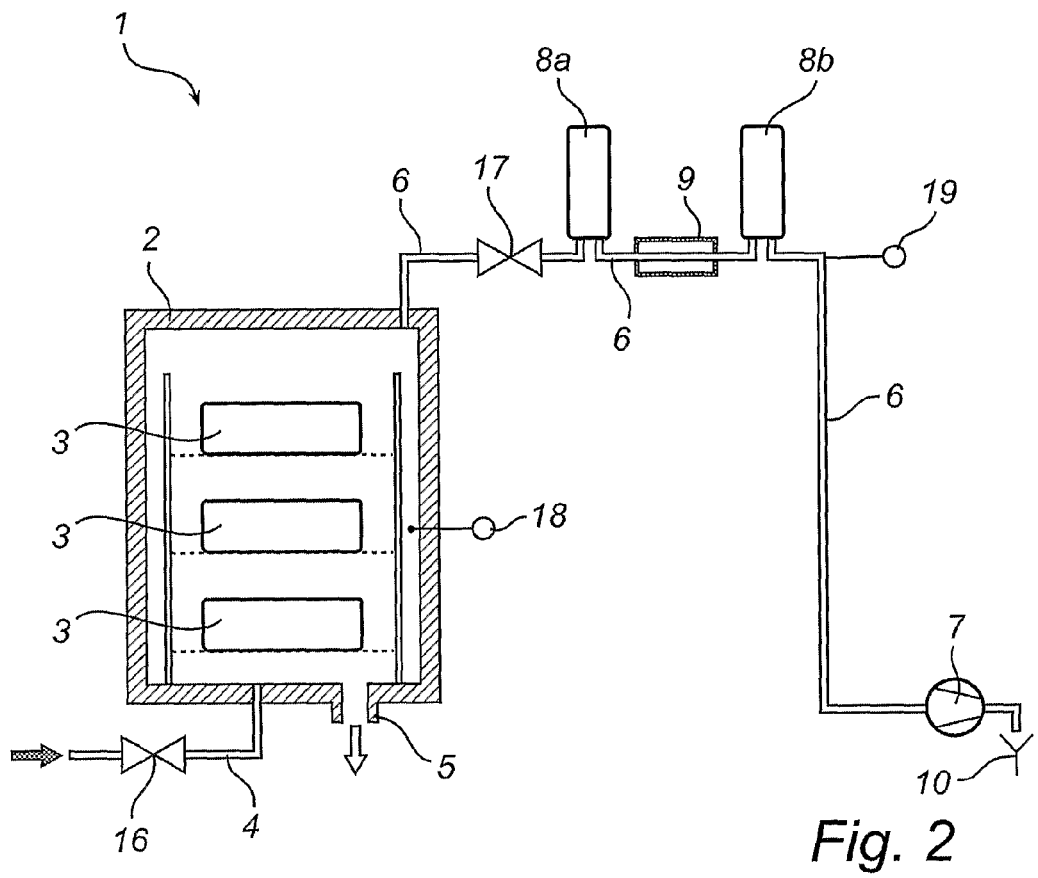
FIG. 2 discloses a schematic drawing showing an autoclave as an embodiment of the invention.

Accordingly to one embodiment FIG. 2 shows how the autoclave 1 may be constructed. The autoclave 1 comprises a chamber 2 into which articles and objects 3 which shall be sterilized and decontaminated are loaded. The chamber 2 has one gas generator (not shown) for example a steam generator connected via a pipe 4 to the lowest point of the chamber 2. However it could be connected elsewhere to the chamber 2. The pipe 4 has a valve 16, which is used to control the steam generator. At the bottom of the chamber 2 is also an exhaust line 5 arranged for enabling condensate, which is produced during the process and which will not be vaporized and which is gathered at the bottom part of the chamber 2, to be emitted after sterilization has taken place. A valve (not shown) keeps the exhaust line 5 closed during the process until the sterilisation process has ended. At the upper region of the chamber 2 another exhaust line 6 is arranged. Through this exhaust line 6 air and/or steam is being exhausted through, by using a vacuum means 7, for example a vacuum pump during the process. The vacuum means 7 is connected to the chamber 2 via the exhaust line 6. To certify that no dangerous organism or viruses can escape via the exhaust line 6 two sterile filters 8a, 8b are arranged in series. However, more than two filters may be arranged in series to increase the safety even further. The vacuum means is arranged after the sterile filters in direction downstream and may be used during the pre-evacuations phase and in the evacuation after the sterilization process. A valve 17 is arranged before the filters 8a, 8b and may separate the chamber from the exhaust line 6 and the filters 8a, 8b.

Condensate will develop within the exhaust line and the filters 8a, 8b when the steam/air from the chamber 2 reaches colder areas. The condensate, which develops before the first filter 8a may drain back to the chamber 2 and the condensate, which develops after the second filter 8b may be drain out into the outlet 10, since it is considered as sterile. However the condensate between the two filters, which are sterile filter, i.e. hydrophobic filters cannot pass through without being vaporised. Sterile filters/hydrophobic filters are filters where steam, gas or air can pass through. So between the two filters 8a and 8b a heating means 9 is arranged to heat the condensate, which develops in the exhaust line 6 between the two filters 8a, 8b, so that the condensate vaporize and can pass the second filter 8b in the downstream direction. The heating means 9 may be a heat exchanger driven by saturated steam or any kind of heat exchanger or any other type of heating device for example an electrical heating device. The filters themselves may be heated to reduce condensate to develop within the filters. Temperature sensors (18, 19) are arranged to the system to control the sterilization temperature in the chamber 2 and in the exhaust line 6.

Figure 3:
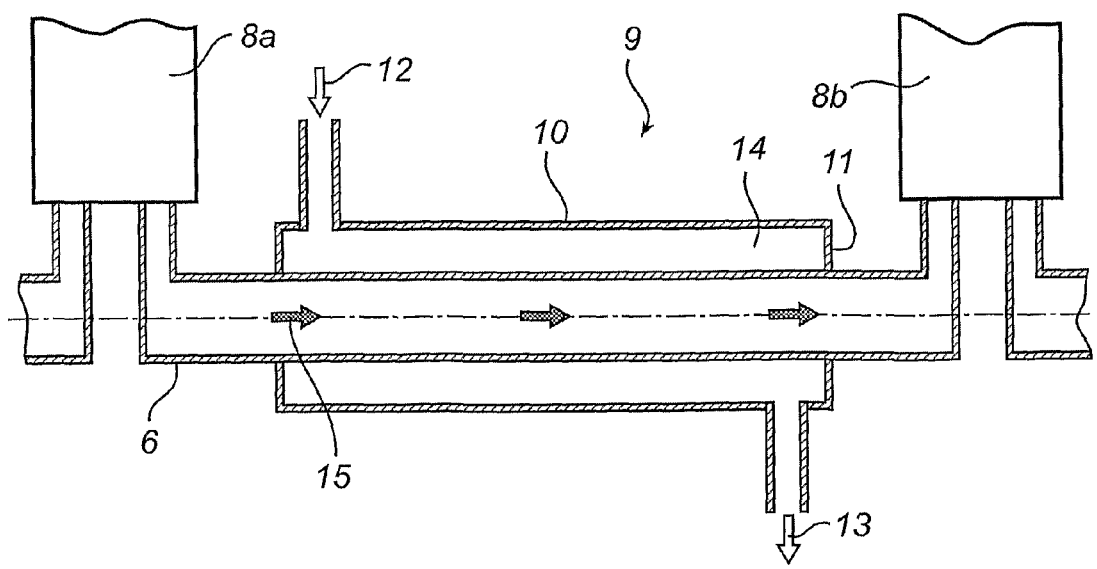
FIG. 3 discloses a schematic drawing showing a part of the autoclave in FIG. 1.

FIG. 3 shows a heat exchanger 9, which works with gas, for example saturated steam. By using the same kind of gas as which is being used in the process within the sterilization device the gas source could be the same. The advantage is that less parts are needed. The heat exchanger comprises a body 10, for example a pipe, which is arranged around the exhaust line 6 coaxial, at least partially. The body 10 creates a housing, through having tightly closed ends 11, with an inner space 14 created between the body 10 and the exhaust line 6. The body is tightly arranged to the exhaust line through for example welding or any other tightly closing arrangement. The closed body 10 may cover the whole exhaust line 6 between the filters 8a, 8b or only some part of it. Preferably is the heat exchanger 9 arranged at the lowest point between the two filters 8a, 8b of the exhaust line 6 where the condensate will be gathered if the exhaust line 6 slopes. The exhaust line may slope so that the condensate easier may run through the system. The aim of the heat exchanger is to heat the condensate until vaporization so that it can pass the sterile filter to become sterile. However, the heat exchanger may be used to sterilize the condensate itself. At one end of the body 10 an inlet 12 for the gas for example saturated steam is arranged and at the other end of the body 10 is an outlet 13 for the steam arranged. The steam is introduced to the system through the inlet 12 and passes through the whole inner space 14 between the exhaust line 6 and the body 10 and thereby heating the condensate lying in the exhaust line so that it can pass the second filter 8b in a down stream direction 15.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A steam sterilization device configured for at least one of sterilization of media or equipment and decontamination of waste material using steam, said steam sterilization device, comprising:
   a chamber connected to an outlet;
   at least one exhaust line arranged between said chamber and the outlet, wherein the at least one exhaust line is configured to evacuate at least one of air and steam from said chamber to said outlet;
   at least two filters arranged in series along said at least one exhaust line between said chamber and said outlet;
   at least one vacuum connected to the chamber via said at least one exhaust line and said at least two filters, wherein the at least one vacuum is configured to evacuate the at least one of air and steam through said at least one exhaust line; and
   at least one heater arranged along said exhaust line between said at least two filters, wherein the at least one heater is configured to vaporize condensate that develops between said at least two filters,
   wherein said at least two filters are hydrophobic sterile filters.

2. The steam sterilization device according to claim 1, wherein said at least one exhaust line is arranged at an upper region of said chamber.

3. The steam sterilization device according to claim 1, wherein said at least one exhaust line is arranged at least above water level in said chamber.

4. The steam sterilization device according to claim 1, wherein said heater is adapted to be shut-off.

5. The steam sterilization device according to claim 1, wherein said heater is a heat exchanger.

6. The steam sterilization device according to claim 1, wherein said heater is an electrical heating device.

7. The steam sterilization device according to claim 1, wherein said heater is arranged at a level where the condensate is gathered between said at least two filters.

8. The steam sterilization device according to claim 1, wherein said at least two filters are essentially of the same type.

9. A sterilization process for at least one of sterilization of media or equipment and decontamination of waste material using at least one vacuum-steam phase within a chamber including an exhaust line, of a sterilization device, comprising the steps of:
   loading the chamber with the media or the equipment to be sterilized or the waste material to be decontaminated;
   pre-evacuating the chamber of air with a vacuum at least once;

introducing steam into the chamber after each pre-evacuation, via an input line connected to a gas generator;

heating the chamber and its content with steam until sterilizing temperature and pressure is attained;

maintaining the steam pressure and temperature until the content of the chamber is sterilized;

evacuating the chamber until the content of the chamber is essentially dry; and equalizing chamber pressure, wherein, during at least said pre-evacuation of said chamber by suction of the air from the chamber, said air is filtered through at least two hydrophobic sterile filters arranged in series, and wherein condensate developed between said two hydrophobic sterile filters is heated by a heater arranged along the exhaust line between said at least two hydrophobic filters to vaporize said condensate between said at least two hydrophobic filters.

* * * * *